United States Patent [19]

Paez

[11] Patent Number: 5,038,764

[45] Date of Patent: Aug. 13, 1991

[54] ORTHOTIC SPLINT

[75] Inventor: Juan B. Paez, Spring Arbor, Mich.

[73] Assignee: Camp International, Inc., Jackson, Mich.

[21] Appl. No.: 453,611

[22] Filed: Dec. 20, 1989

[51] Int. Cl.$^5$ .............................................. A61F 5/04
[52] U.S. Cl. ................................. 128/87 A; 128/87 R
[58] Field of Search .............. 128/26, 69, 87 R, 87 A, 128/94; 2/1.1, 16, 21, 163

[56] References Cited

U.S. PATENT DOCUMENTS

| 2866440 | 12/1958 | Green | 434/166 |
|---|---|---|---|
| 4,220,334 | 9/1980 | Kanamoto et al. | 128/26 |
| 4,243,026 | 1/1981 | Barber | 128/87 A |
| 4,297,992 | 11/1981 | Larue et al. | 128/87 A |
| 4,441,489 | 4/1984 | Evans et al. | 128/87 A |
| 4,456,002 | 6/1984 | Barber et al. | 128/87 A |
| 4,657,000 | 4/1987 | Hepburn | 128/87 R |
| 4,665,905 | 5/1987 | Brown | 128/87 R |
| 4,702,474 | 10/1987 | Guibert | 272/122 |
| 4,944,290 | 7/1990 | Hepburn | 128/87 A |

FOREIGN PATENT DOCUMENTS

| 3444286 | 6/1986 | Fed. Rep. of Germany .... 128/87 R |
| 2616061 | 12/1988 | France ............................. 128/87 R |

OTHER PUBLICATIONS

"Force Magnitude of Commercial Spring-coil and Spring-wire Splints Designed to Extend the Proximal Interphalangeal Joint," Journal of Hand Therapy, Jan.-Mar. 1988, pp. 86-90.

Pp. 134 and 135 from the J.A. Preston Corporation catalog, "Guidelines for use of LMB Orthoses," published by LMB Hand Rehab Products, Inc.

Primary Examiner—Robert A. Hafer
Assistant Examiner—Charles H. Sam
Attorney, Agent, or Firm—Price, Heneveld, Cooper, DeWitt & Litton

[57] ABSTRACT

A compact, unobtrusive orthotic splint comprising length adjustable padded malleable cuffs for positioning along and fastening to the splint, and an accordion-style spring to provide controlled extension or flexion.

23 Claims, 3 Drawing Sheets

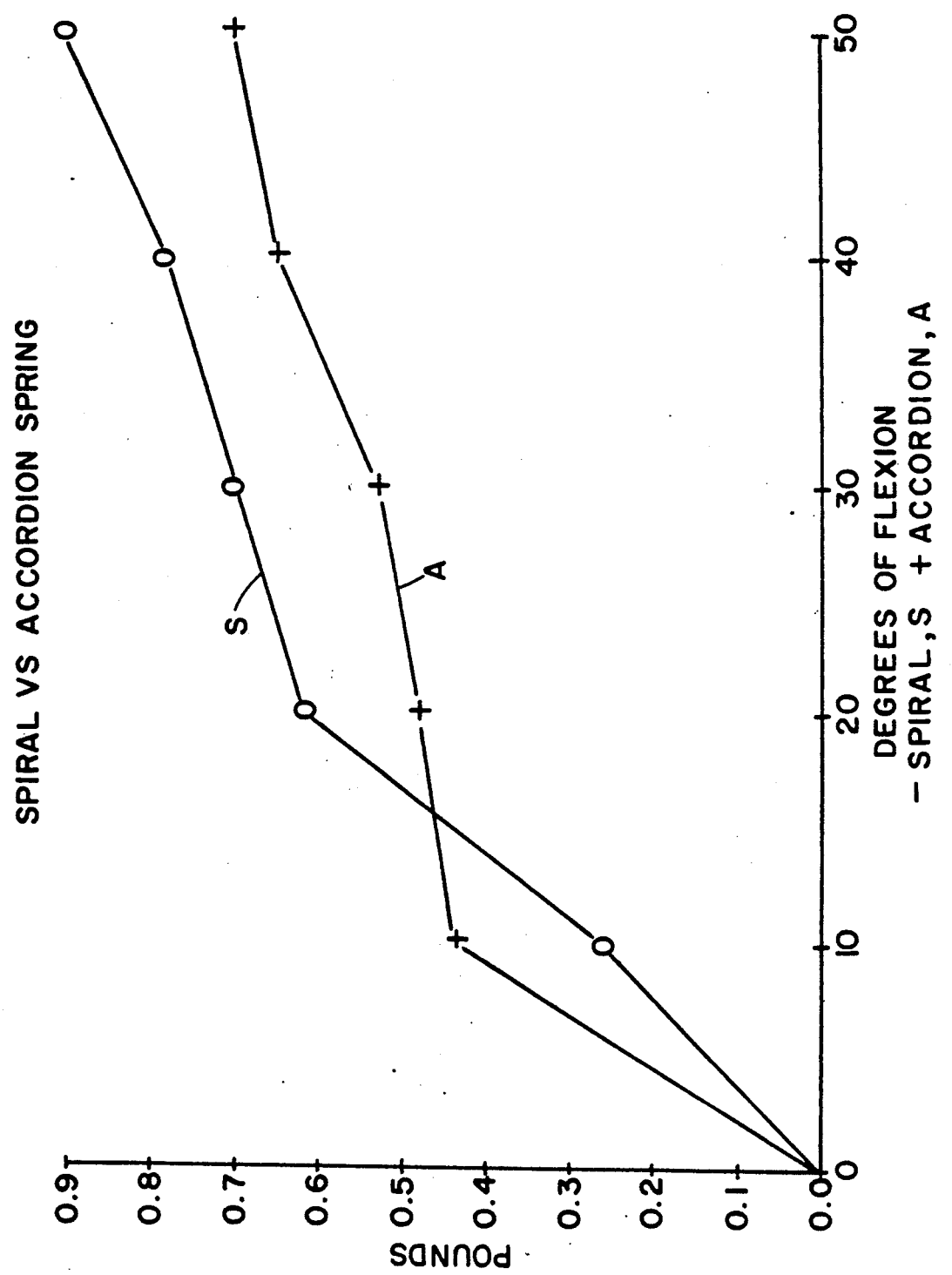

ORTHOTIC SPLINT

BACKGROUND OF THE INVENTION

The present invention relates to the specific medical area of orthotics and more particularly with regard to extension and flexion extremity splints.

Frequently, in the rehabilitative treatment of arthritic, stroke or accident patients presenting neurological, muscular, joint or tendon damage regarding an extremity, it is desirable to splint the affected extremity such that a controlled movement is allowed or encouraged. The controlled movement might be against a specified resistive force or might be with a specific force applied to encourage a desired deflection or movement. The ultimate goal of the therapy is to restore mobility of the extremity to a state as near normal as is possible and to do so within a reasonable time. Some of the practical or desirable characteristics or limitations of such splints include the splint should not restrict other extremities; the weight of the splint should be minimized to enhance comfort and therapeutic effectiveness; the splint should be compact to minimize the intrusion of the splint, both functionally and cosmetically; the splint should be sufficiently durable to endure the course of treatment without undue deference by the patient; the splint should be comfortable; the splint should be easy to use; and the potential for the patient to avoid using the splint should be minimized.

Many splints currently available typically use conspicuous, awkward or bulky strapping means for positioning or fastening. Further, they often use protruding wires and hooks. The use of elastic bands, coil springs, and springy wires is commonplace in the current market. However, these tensioning means have specific limitations. The use of elastic bands mandates the use of hooks and protruding levers. Coil springs and springy wires have a limited range of useful force and once outside such range the applied force rapidly exceeds desired and safe levels or quickly decreases from required levels It should be noted that an excessive force might cause additional damage rather than curing, while insufficient force may result in a protracted or ineffective rehabilitative treatment.

SUMMARY OF THE INVENTION

The orthotic device of the present invention includes an accordion-style spring. This spring has unique force characteristics as compared with the traditional springy wire or coil spring. The accordion spring has a significantly flatter force curve, offering a broader range of useable application The accordion spring also offers a more compact configuration so it is less intrusive and enhances the fitting process. Besides having a flatter force response to deflection, the accordion spring offers a broader range of force values, making the implementing splint adaptable to a wider range of applications.

In another aspect of the invention, the splint of the present invention readily accommodates the fitting process by using adjustable cuffs and adjustable length. This enables the same device to fit different-sized users.

These and other aspects, objects and features of the invention will be more readily understood and appreciated by reference to the written specification and appended drawings.

BRIEF DESCRIPTION OF THE DRAWINGS

FIG. 6 shows the spring rate curve for a splint made in accordance with the present invention to that for a prior art spiral spring (Capener) splint.

DESCRIPTION OF THE PREFERRED EMBODIMENT

The splint of the present invention is specifically applicable to the splinting of a finger in extension, but is not limited to this specific application and is intended in alternative configurations for use with other extremities in extension or flexion.

Figure 1:
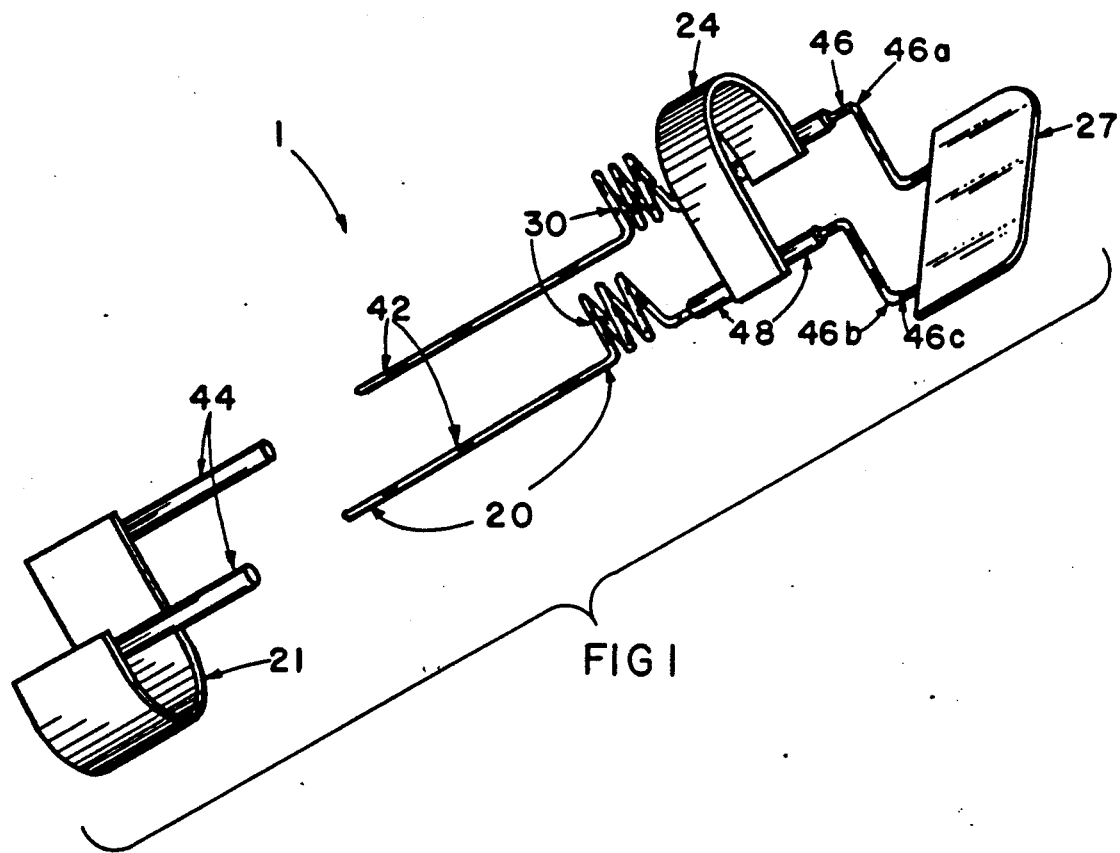
FIG. 1 shows an exploded perspective of the invention embodied in a finger extension splint with slidable tip cuff detached.
Figure 2:
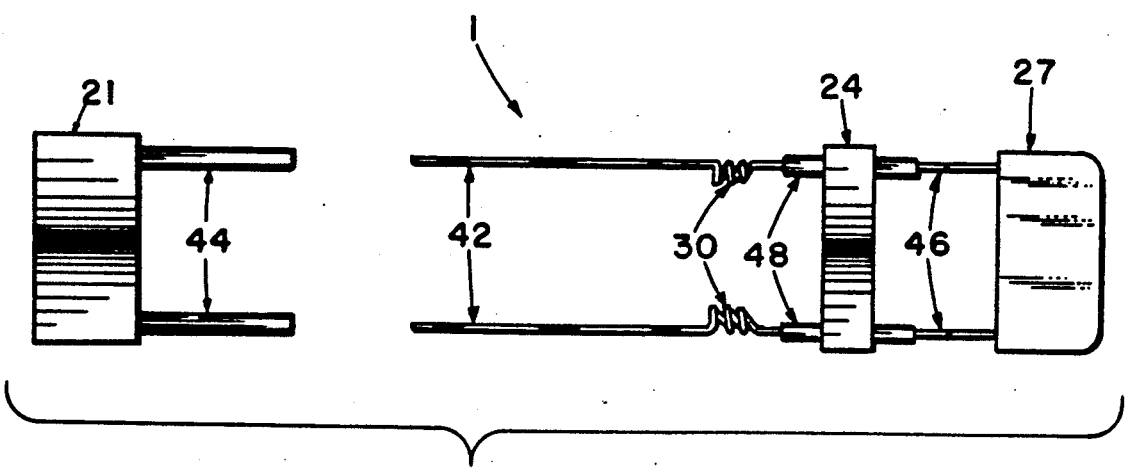
FIG. 2 shows a plan view of the FIG. 1 splint.
Figure 3:
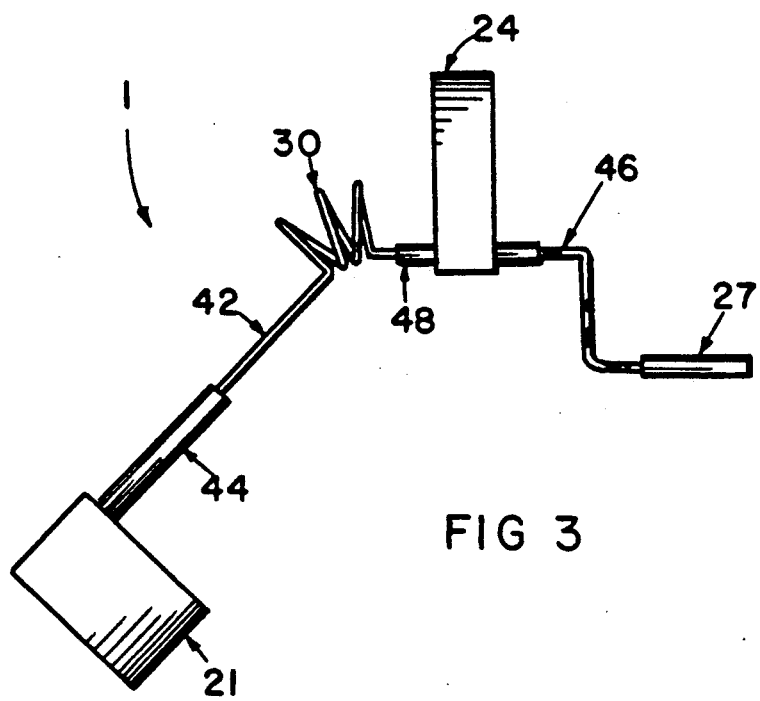
FIG. 3 shows a side elevation of the FIG. 1 splint deflected.

Referring to FIGS. 1, 2 and 3, splint 1 comprises a pair of spaced, generally parallel side members 20 which lie in generally parallel reference planes Each side 20 is formed of a piece of spring steel rod or wire to define an accordion spring 30 having a forward projecting sizing rod 42 and a rear projecting sizing rod 46. Each rear projecting rod 46 is bent at 46a and 46b such that the rear extremity portion 46c of rod 46 is generally parallel to, but offset from, the forward portion of rod 46 adjacent spring 30.

A tip cuff 21 is slidably mounted on rods 42. Cuff 21 comprises a padded malleable metal strap which is attached at each end to sizing tubes 44. Tubes 44 slide telescopically on sizing rods 42 so that the effective length of splint 1 can be adjusted.

A mid-cuff 24 is slidably mounted on rear rods 46. Like cuff 21, mid-cuff 24 is also a padded malleable metal strap attached at each end to sizing tubes 48. Tubes 48 slide along rods 46 so that the position of mid-cuff 24 can be adjusted.

A third cuff 27, also a padded malleable metal strap, is fixedly secured to the ends of rods 46. Cuff 27 holds sides 20 in their generally parallel configuration. Bends 46a and 46b in rods 46 position cuff 27 in the distal area of the palm of the hand proximal to the first joint of the affected finger.

Each accordion spring 30 is formed by bending a spring steel rod or wire, preferably stainless steel, into a wave-like configuration defining a series of peaks and valleys. Spring 30 is not merely planar in its dimensions, however Rather, it has a slight lateral dimension, being bent into the shape of a flattened helix, as for example a spiral circumscribed on the surface of a flat bar (see FIGS. 1 and 2).

Splint 1 is fitted to and sized to a patient by a therapist. After proper fitting and sizing, cuffs 21 and 24 may each be fixed at their respective positions by crimping or gluing their respective sizing tubes 44 and 48 to their respective rods 42 and 46, precluding further sliding along their respective rods 42 and 46.

In use, cuffs 24 and 27 will act in combination to form a base from which springs 30 may exert an extending force through cuff 21 against a distal area of the affected finger Splint 1 is applied by deflecting cuff 21 (FIG. 3) and inserting the affected finger between cuffs 24 and 27 and between rods 46 such that cuff 24 moves over the top of the finger until cuff 27 becomes positioned at a distal area of the palm of the hand proximal to the first joint of the affected finger and said finger projects between springs 30 and rods 42. Then cuff 21 is gently released to exert pressure against a distal area of said finger. With splint 1 in position and released, springs 30 exert a springing action developing forces acting normally to the inside face of each cuff 21, 24 and 27, resulting in splint 1 encouraging an extension of the finger.

FIG. 6 shows the spring rate curve for a prior art Capener splint and a splint made in accordance with the present invention. Torque in pounds is plotted on the ordinant and degrees of flexion are plotted on the abscissa. As can be seen, the rate curves for the spiral spring Capener splint is generally greater for a given degree of flex, indicating that progressively greater force is required to achieve a greater degree of flexion The spring rate curve for the splint of the present invention is lower, such that the continuing application of an even force results in continued deflection of the splint at approximately the same, even rate. This allows one to change the orientation of the extremity over a wide range of movement without having to increasingly strain the extremity to do so.

Figure 4:
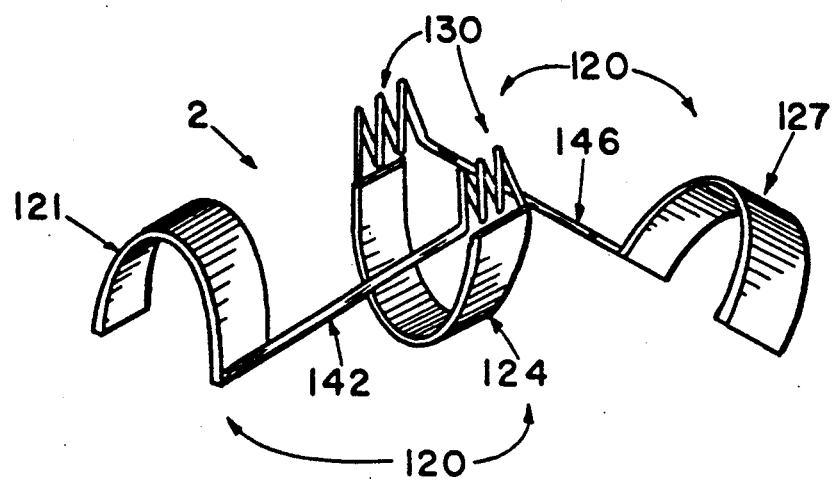
FIG. 4 shows a perspective of the invention embodied as a finger flexion splint.
Figure 5:
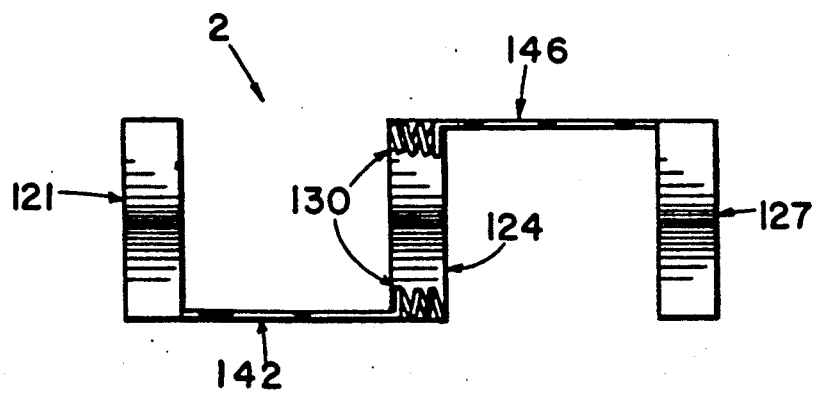
FIG. 5 shows a plan view of the FIG. 4 splint.

In the alternative, splint 2 (FIGS. 4 and 5) comprises two sides 120, also located in spaced, generally parallel reference planes. Each side 120 is formed of spring steel to define an accordion spring 130, one of which has a forward projecting rod 142 and the other of which has a rear projecting rod 146. Cuff 121, like cuff 21, comprises a padded, malleable metal strap which is connected at one end to forwardly projecting rod 142 Cuff 121 projects laterally from the end of forwardly projecting rod 142 towards the spaced parallel plane of the opposite side 120 of splint 2.

Mid-cuff 124 also comprises a piece of padded, malleable metal. Mid-cuff 124 is connected at one end to the end of accordion spring 130 on one side 120 of splint 2 and extends laterally therefrom towards the reference plane of opposite side 120 where its other end is fixedly secured to the end of accordion spring 130 of said opposite side 120. In this way, mid-cuff 124 forms a bridge between the opposite sides 120 of splint 2 and fixes their spatial relationship with respect to one another.

Rear cuff 127 also comprises a padded, malleable metal strap. Cuff 127 is secured at one end to rearwardly projecting rod 146 and projects laterally therefrom back towards the reference plane of side 120 in which forwardly projecting rod 142 is located.

Sides 120, and specifically rod portions 142 and 146, are oriented at an angle to one another, when splint 2 is viewed in side elevation. They define an included angle, in their "at rest" position of less than 180°, and more specifically about 135°. Cuffs 121 and 127 curve arcuately away from their respective sides 120 in a direction away from the included angle, while mid-cuff 124 curves in the direction of the included angle. These cuff configurations and said included angle make splint 2 useful as a flexion splint as distinguished from an extension splint.

Each spring 130 has a configuration the same as that of each spring 30, described above. In use, cuff 127 is positioned over the finger between the first and second joints, cuff 124 is positioned under the second joint of the finger and cuff 121 is positioned over the finger between the second and third joints Once applied, the spring action of springs 130 develop forces acting normally to the inside surfaces of cuffs 127, 124 and 121, tending to move cuff 124 upward in relation to cuffs 121 and 127 while cuffs 121 and 127 tend to move downward in relation to cuff 124 and the affected finger is biased towards flexion.

A significant advantage of flexion splint 2 is that the accordion springs 130 still operate in tension as the user changes the position of his or her extremity Prior art flexion splints operate in compression In other words, as one attempts to straighten one's finger from the flexed position, one compresses the spring members located along the sides of the splint. In contrast, the accordion springs 130 of splint 2 are placed in tension as the user straightens his or her flexed extremity, in the same manner that accordion springs 30 of extension splint 1 are placed in tension when the user flexes his or her extremity.

This is important in that spring rates tend to increase very rapidly in the compression of a spring as opposed to its extension. Thus, a great deal of force has to be exerted to straighten one's extremity when using a prior art flexion splint.

In contrast, the flexion splint 2 of the present invention places its side springs 130 in tension as a user straightens his or her finger. Flexion splint 2 thus exhibits the same relatively flat spring torque rate as a user straightens his or her finger, as is experienced by accordion springs 30 in extension splint 1 when a user flexes his or her extremity from the extended position.

While the Figures and the description of the preferred embodiments refer to the specific application of the invention to the extension and flexion of a finger, the invention is not intended to be limited to such specific application, used for descriptive purposes, but is intended to be generally applicable to active splinting of body extremities in flexion or extension.

The above description is considered that of the preferred embodiments only. Modifications of the invention will occur to those who make or use the invention. Therefore, it is understood that the embodiments shown in the drawings and described above are merely for illustrative purposes and are not intended to limit the scope of the invention, which is defined by the following claims.

The embodiments of the invention in which an exclusive property or privilege is claimed are defined as follows.

1. An orthotic splint comprising:
a first side member extending generally along a first longitudinal axis, located generally in a first reference plane and having a first end;
a second side member extending generally along a second longitudinal axis, located generally in a second reference plane and having a first end, said reference planes being generally parallel and laterally spaced from one another whereby said first side member will be located on one side of a body part to be splinted and said second side member will be located on the opposite side of such body part, said first ends of said side members being spaced longitudinally from one another, relative to said axes, to thereby generally define the longitudinally opposite ends of said splint;
a first body engaging cuff having a first end connected to said first side member near said first end of said first side member and projecting generally toward said second reference plane;
a second body engaging cuff having a first end connected to said second side member near said first end of said second side member and projecting generally toward said first reference plane;

a medial cuff located between said first and second cuffs, extending between said first and second side members and having first and second ends connected to said first and second side members, respectively;

at least one of said side members including an accordion spring located between one of said first and second cuffs and said medial cuff whereby said splint is given a biased spring action forced by said accordion spring, said accordion spring comprising a resilient, springy material defining a rod configured over a portion of its length in a wave-like configuration defining a series of peaks and valleys extending generally along the longitudinal axis of the side member.

2. The splint of claim 1 wherein said first cuff has a second end located generally in said second plane, said second side member has a second end longitudinally opposite said first end of said second side member and said second end of said first cuff is connected to said second end of said second side member.

3. The splint of claim 2 wherein at least one of said first and second cuffs is connected to its respective side member by length-adjusting means whereby said cuff can be positioned at a plurality of positions along said side member to adjust the relative longitudinal position of said cuff.

4. The splint of claim 3 wherein said length adjusting mean is a tubular sleeve slideably circumscribing said side member and said cuff is connected to said sleeve so that said cuff and said sleeve are slideably movable along the length of said side member to adjust the relative longitudinal position of said cuff.

5. The splint of claim 4 wherein said sleeve is crimpable to preclude further slideability thereafter and fix the longitudinal position of said cuff.

6. The splint of claim 2 wherein said second cuff has a second end located generally in said first plane, said first side member has a second end longitudinal opposite said first end of said first side member, said second end of said second cuff is connected to said second end of said first side member and each of said first and second side members includes an accordion spring.

7. The splint of claim 6 wherein at least one of said first, second and medial cuffs is connected to said first and second side members by length-adjusting means whereby said cuff can be positioned at a plurality of positions along said side members to adjust the relative longitudinal position of said cuff.

8. The splint of claim 7 wherein said length adjusting means is a tubular sleeve slideably circumscribing said side member and said cuff is connected to said sleeve so that said cuff and said sleeve are slideably movable along the length of said side member to adjust the relative longitudinal position of said cuff.

9. The splint of claim 11 wherein said sleeve is crimpable to preclude further slideability thereafter and fix the longitudinal position of said cuff.

10. The splint of claim 1 wherein said accordion spring defines a helix, said helix having an axis and said axis being generally parallel to the axis of said side member, said spring action force being developed by longitudinal deflection of said accordion spring.

11. The splint of claim 10 wherein said helix of said accordion spring is a flattened helix to define said peaks and valleys and said flattened helix is substantially within said reference plane of said side member.

12. An orthotic splint comprising:

a first side member extending generally along a first longitudinal axis, located generally in a first reference plane and having a first end;

a second side member extending generally along a second longitudinal axis, located generally in a second reference plane and having a first end, said reference planes being generally parallel and laterally spaced from one another whereby said first side member will be located on one side of a body part to be splinted and said second side member will be located on the opposite side of such body part, said first ends of said side members being spaced longitudinally from one another, relative to said axes, to thereby generally define the longitudinally opposite ends of said splint;

a first body-engaging cuff having a first end connected to said first side member near said first end of said side member and projecting generally toward said second reference plane;

a second body-engaging cuff having a first end connected to said second side member near said first end of said second side member and projecting generally toward said first reference plane;

a medial cuff located between said first and second cuffs, extending between said first and second side members and having first and second ends connected to said first and second side members, respectively;

at least one of said first and second cuffs being connected to its respective side member by length-adjusting means whereby said cuff can be positioned at a plurality of positions along said side member to adjust the relative longitudinal position of said cuff;

at least one of said side members including an accordion spring located between one of said first and second cuffs and said medial cuff whereby said splint is given a biased spring action force by said accordion spring, said accordion spring comprising a resilient, springy material defining a rod configured over a portion of its length in wave-like configuration defining a series of peaks and valleys extending generally along the longitudinal axis of said side member.

13. The splint of claim 12 wherein said length adjusting means is a tubular sleeve slideably circumscribing said side member and said cuff is connected to said sleeve so that said cuff and said sleeve are slideably movable along the length of said side member to adjust the relative longitudinal position of said cuff.

14. The splint of claim 13 wherein said sleeve is crimpable to preclude further slideability thereafter and fix the longitudinal position of said cuff.

15. The splint of claim 12 wherein said accordion spring defines a helix and said spring action force is developed by longitudinal deflection of said accordion spring.

16. An orthotic splint comprising:

a first side member extending generally along a first longitudinal axis, located generally in a first reference plane and having first and second ends;

a second side member extending generally along a second longitudinal axis, located generally in a second reference plane and having a first end opposite said first end of said first side member and a second end opposite said second end of said first side member, said reference planes being generally parallel and laterally spaced from one another whereby said first side member will be located on one side of a body part to be splinted and said second side member will be located on the opposite side of such body part, said first and second ends of each said side member generally defining the longitudinally opposite ends of said splint;

a first body-engaging cuff arcuately extending between and connected to said side members near said first ends of said side members so that said first cuff is concave in one direction and convex in an opposite direction thereto;

a second body-engaging cuff arcuately extending between and connected to said side members near said second ends of said side members so that said second cuff is concave in the same general direction as said first cuff; and a medial cuff located between said first and second cuffs, arcuately extending between and connected to said first and second side members so that said medial cuff is concave in the direction opposite to the direction in which said first and second cuffs are concave;

said first cuff and said medial cuff being connected to said side members by length-adjusting means whereby said cuffs can be positioned at a plurality of positions along said side members to adjust the relative longitudinal position of said cuffs;

each of said side members including an accordion spring located between one of said first and second cuffs and said medial cuff whereby said splint is given a biased spring action force by said accordion spring, said accordion spring comprising a resilient, springy material defining a rod configured over a portion of its length in a wave-like configuration defining a series of peaks of valleys extending generally along the longitudinal axis of the side member, said spring action force being developed by longitudinal deflection of said accordion spring.

17. The splint of claim 16 wherein each said length-adjusting means is a tubular sleeve slideably circumscribing said side member and each said cuff is connected to said sleeves so that each said cuff and said sleeves are slideably movable along the length of said side member to adjust the relative longitudinal position of each said cuff.

18. The splint of claim 17 wherein said sleeve is crimpable to preclude further slideability thereafter and fix the longitudinal position of said cuff.

19. An orthotic splint comprising:
a first side member extending generally along a first longitudinal axis, located generally in a first reference plane and having a first end and a second end;
a second side member extending generally along a second longitudinal axis, located generally in a second reference plane and having a first end and a second end, said reference planes being generally parallel to and laterally spaced from one another whereby said first side member will be located on one side of a body part to be splinted and said second side member will be located on the opposite side of such body part, said first ends of said side members being spaced longitudinally from one another, relative to said first and second longitudinal axes, to thereby generally define the longitudinally opposite ends of said splint, said second ends of said side members being located generally opposite each other across said body part to be splinted, said axes being angularly oriented relative to one another to define an included angle of less than 180°;

a medial body-engaging cuff arcuately extending between and connected to said side members near said second ends of said side members so that said cuff extends arcuately away from said side members;

a first body-engaging cuff having a first end connected at said first end of said first side member and arcuately projecting laterally from said first side member generally toward said second reference plane so that the arc of said first cuff is generally inverse to the arc of said medial cuff;

a second body-engaging cuff having a first end connected at said first end of said second side member and arcuately projecting laterally from said second side member generally toward said first reference plane so that the arc of said second cuff is generally inverse to the arc of said medial cuff; and at least one of said side members including an accordion spring located between one of said first and second cuffs and said medial cuff whereby said splint comprises a flexion splint tending to hold the user's extremity in flexion and whereby said accordion spring is placed in tension as the user extends his or her extremity, said accordion spring comprising a resilient, springy material defining a rod configured over a portion of its length in a wave-like configuration defining a series of peaks and valleys extending generally along the longitudinal axis of the side member, said tension developing by a longitudinal deflection of said accordion spring.

20. The splint of claim 19 in which each of said first and second side members include an accordion spring, said accordion spring on said first side member being located between said medial cuff and said first cuff and said accordion spring on said second side member being located between said medial cuff and said second cuff.

21. The splint of claim 20 in which each said accordion spring includes an end defining the second end of its respective side member, said connection of said medial cuff to each of said side members being at said ends of said accordion springs.

22. The splint of claim 19 wherein said said accordion spring defines a flattened helix comprising a series of interconnected coils which are taller than they are wide to minimize the width of said accordion spring, which are located generally in the respective reference plane of the side member and the tops and bottoms of which define a series of peaks and valleys along a portion of the length of the side member.

23. The splint of claim 1 wherein said spring action force remains substantially constant over the therapeutic range of motion of said orthotic splint.

* * * * *

UNITED STATES PATENT AND TRADEMARK OFFICE
CERTIFICATE OF CORRECTION

PATENT NO. : 5,038,764

DATED : August 13, 1991

INVENTOR(S) : Juan B. Paez

It is certified that error appears in the above-identified patent and that said Letters Patent is hereby corrected as shown below:

Column 1, Line 43:

After "levels" insert --.--

Column 1, Line 54:

After "application" insert --.--

Column 2, Line 53:

After "however" insert --.--

Column 2, Line 66:

After "finger" insert --.--

Column 3, Line 18:

After "curve" insert --A--.

Column 4, Line 7:

After "extremity" insert --.--

Column 4, Line 8:

After "compression" insert --.--

Column 5, Claim 4, Line 31:

"mean" should be --means--

UNITED STATES PATENT AND TRADEMARK OFFICE
CERTIFICATE OF CORRECTION

PATENT NO. : 5,038,764
DATED : August 13, 1991
INVENTOR(S) : Juan B. Paez

It is certified that error appears in the above-identified patent and that said Letters Patent is hereby corrected as shown below:

Column 5, Claim 9, Line 59:

"claim 11" should be --claim 8--

Signed and Sealed this

Twenty-first Day of December, 1993

Attest:

BRUCE LEHMAN

Attesting Officer

Commissioner of Patents and Trademarks